(12) United States Patent
Whang

(10) Patent No.: US 7,559,944 B2
(45) Date of Patent: Jul. 14, 2009

(54) HAIR GROWTH APPARATUS

(76) Inventor: Ha-Uk Whang, A-401, Joheung Billa, 316-44, Sang-Dong, Wonmi-Gu, Bucheon-Si, Gyeonggi-Do (KR) 420-180

( * ) Notice: Subject to any disclaimer, the term of this patent is extended or adjusted under 35 U.S.C. 154(b) by 56 days.

(21) Appl. No.: 10/546,701

(22) PCT Filed: Feb. 26, 2004

(86) PCT No.: PCT/KR2004/000408

§ 371 (c)(1),
(2), (4) Date: Aug. 24, 2005

(87) PCT Pub. No.: WO2004/075978

PCT Pub. Date: Sep. 10, 2004

(65) Prior Publication Data

US 2006/0142823 A1    Jun. 29, 2006

(30) Foreign Application Priority Data

Feb. 26, 2003    (KR) .................. 10-2003-0011896

(51) Int. Cl.
*A61N 1/18* (2006.01)
(52) U.S. Cl. ......................................... 607/88; 606/9
(58) Field of Classification Search ............ 607/88–91; 606/9
See application file for complete search history.

(56) References Cited

U.S. PATENT DOCUMENTS

| | | | | |
|---|---|---|---|---|
| 2,655,145 A | * | 10/1953 | Guillaume | 601/17 |
| 2,699,771 A | * | 1/1955 | Ruttger-Pelli | 601/15 |
| 4,765,316 A | * | 8/1988 | Marshall | 601/70 |
| 5,259,380 A | * | 11/1993 | Mendes et al. | 607/115 |
| 6,024,100 A | * | 2/2000 | Fukuyama | 132/200 |
| 6,080,127 A | * | 6/2000 | Li et al. | 604/22 |
| 6,666,878 B2 | * | 12/2003 | Carlgren | 607/91 |
| 2002/0128696 A1 | * | 9/2002 | Pearl et al. | 607/89 |
| 2003/0028069 A1 | * | 2/2003 | Santiago | 600/9 |

FOREIGN PATENT DOCUMENTS

| | | | |
|---|---|---|---|
| EP | 1 138 349 A3 | | 4/2001 |
| GB | 2160427 A | * | 12/1985 |
| GB | 2167667 A | * | 6/1986 |
| JP | 2-29253 A | | 1/1990 |
| JP | 410005306 A | * | 1/1998 |
| JP | 10-216185 A | | 8/1998 |
| JP | 2002-000742 | | 1/2002 |
| KR | 1998-019587 | | 6/1998 |
| KR | 2002-0013242 | | 2/2002 |

* cited by examiner

*Primary Examiner*—Henry M Johnson, III
*Assistant Examiner*—Lynsey Crandall
(74) *Attorney, Agent, or Firm*—Harness, Dickey & Pierce, P.L.C.; Anthony G. Fussner; Kisuk Lee

(57) ABSTRACT

The present invention relates to a hair growth caring apparatus that includes a head housing, a head pin protruded from a lower side of the head housing, a power generation device fixed to a lower side of the head pin for thereby generating power, a light generation device for generating light, and a heat generation device capable of generating heat, thus preventing the side effects of an artificial depilation agent or transplantation of hair in such a manner that electric energy and light energy are supplied to hair fallen portions, so that it is possible to achieve a natural hair growth for depilation patient.

5 Claims, 4 Drawing Sheets

HAIR GROWTH APPARATUS

TECHNICAL FIELD

The present invention relates to a hair growth caring apparatus, and in particular to a hair growth caring apparatus capable of naturally curing a depilation patient and preventing a depilation phenomenon.

BACKGROUND ART

Generally, hair loss (hair depilation) is caused by heredity, stress, an unbalanced diet, cosmetics, shampoo, hair gel, dying agents and an over use of other chemical agents. As capillaries are contracted, nutrition and oxygen are not fully supplied to the hair roots. Eventually, hair loss occurs.

Various depilation prevention agents have been developed for preventing hair depililation and for promoting hair growth. However, hair growth agents are applied using hands or brushes. Since hair growth agents may be caustic, they need to be handled carefully. For the case where an agent is applied with an unclean hand, various bacteria in the hands are mixed with the hair growth agent, thereby infecting the skin tissue, and causing skin diseases.

In addition, when hair growth agents are taken, various side effects may occur and health may be damaged. If a skin disease occurs, it may be impossible to achieve satisfactory hair growth.

In order to overcome the above problems, a hair transplantation method was developed. However, with a hair transplantation method, since the hairs are transplanted one by one, even though the cost is greater and a long therapy time is needed, a desired effect is only temporarily achieved. Namely, it is impossible to achieve a permanent effect for the depilation.

BRIEF SUMMARY OF THE INVENTION

Accordingly, it is an object of the present invention to overcome the above-described problems encountered in the convention art.

It is another object of the present invention to provide a hair growth caring apparatus capable of promoting a natural growth of hair and of achieving the desired hair therapy without using a depilation prevention agent or a hair transplantation method.

It is a further object of the present invention to provide a hair growth apparatus capable of removing various waste materials, activating blood circulation and preventing various bacteria such that a vibration massage effect and anion are provided to the hair.

To achieve the above objectives in the present invention, a waterway is provided in a touch panel, so that water is received through a pipe for cooling the touch panel. A magnetic force generator is further provided in a head pin for generating magnetic force. A suction port is provided in the touch panel for sucking foreign substances from the hair using the pressure of a pump. A plurality of nozzles are provided in a lower side of the head housing. The nozzles provides anion air/oxygen generator to the user's hair through a flow pipe. A vibrator is provided in an upper side of the head housing.

BRIEF DESCRIPTION OF THE DRAWINGS

The preferred embodiments of the present invention will be described with reference to the accompanying drawings.

BEST MODE FOR CARRYING OUT THE INVENTION

Figure 1:
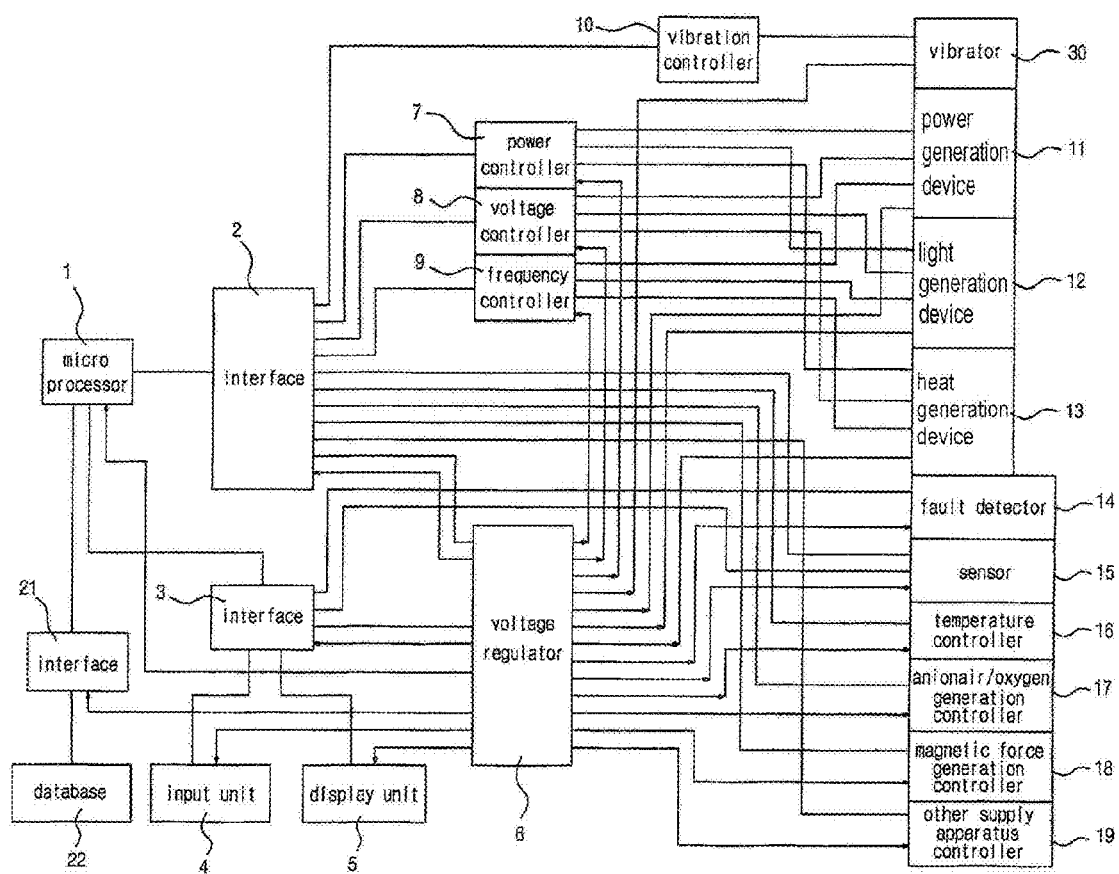
FIG. 1 is a circuit block diagram of a hair growth caring apparatus according to the present invention.
Figure 2:
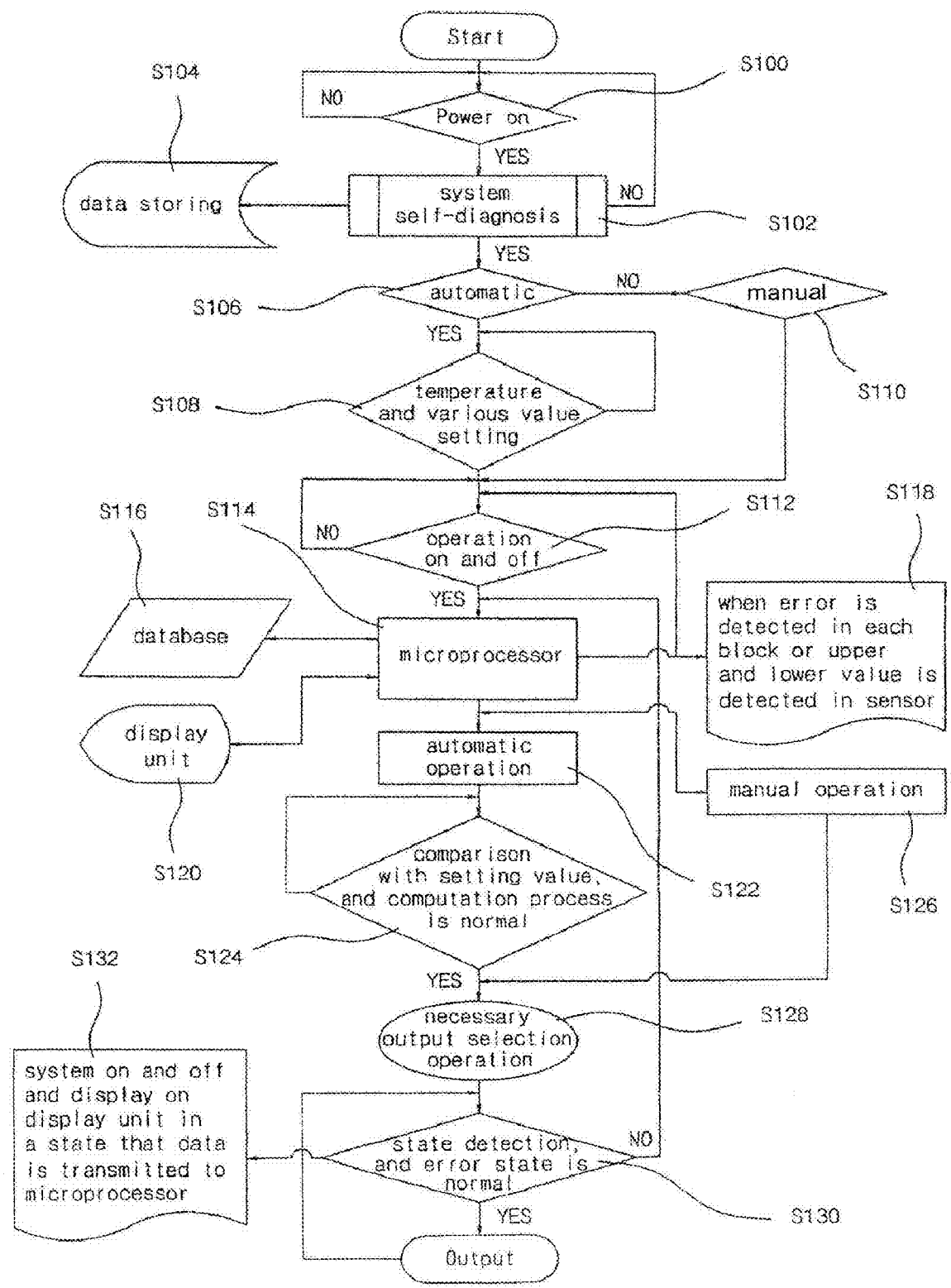
FIG. 2 is a flow chart of a microcomputer control of a hair growth caring apparatus according to the present invention.

The preferred embodiments of the present invention will be described with reference to the accompanying drawings. FIG. 1 is a circuit block diagram of a hair growth caring apparatus according to the present invention, FIG. 2 is a flow chart of a microcomputer control of a hair growth caring apparatus according to the present invention and FIG. 3 is a lateral view of a hair growth caring apparatus according to the present invention.

Figure 3:
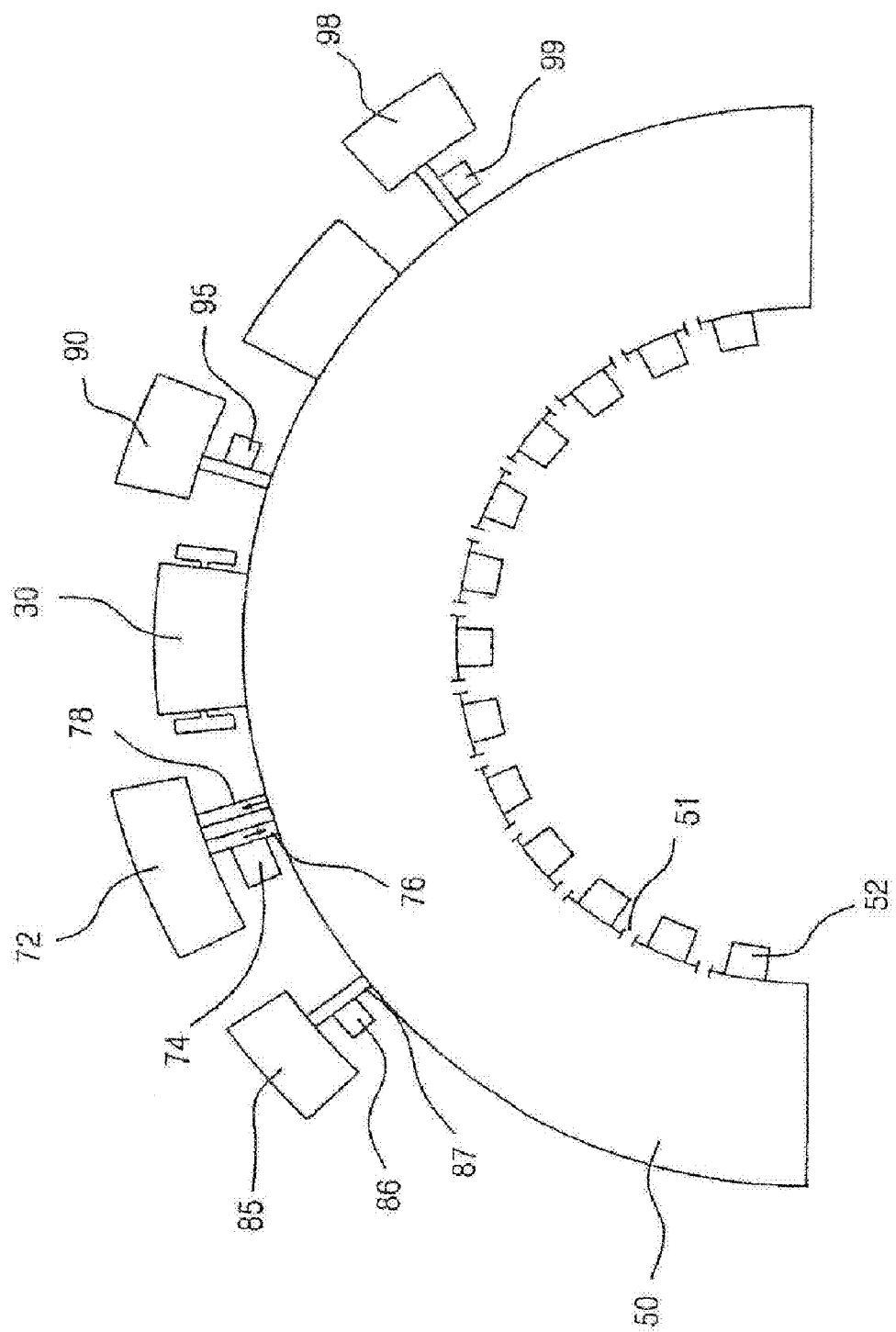
FIG. 3 is a lateral view of a hair growth caring apparatus according to the present invention.

As shown in FIG. 3, a head housing 50 is integrally formed with a plurality of head pins 52 provided in a lower side of the heating housing 50. The head pins 52 contact with a user's head, thus promoting hair growth in a user.

As shown in FIG. 1, a microprocessor 1 performs a stored program based on the inputs from interfaces 3 and 21. As a result, when the signals are transmitted to the interfaces 1, 3, and 21, respectively, a signal corresponding to each block is generated.

The interface 3 converts an output signal from the microprocessor into a signal needed in a display unit 5, classifies the input and output signals from each block, and converts into the signals needed in each block.

The interface 3 also converts data received on input unit 4 from a switch or remote devices into signals that will be processed by the microprocessor 1. The microprocessor 1 processes this data and displays the signals on the display unit 5.

The display unit 5 displays various input data from the input unit 4 and a system operation state, an operation state, etc. in the whole parts of the system.

A voltage regulator 6 supplies a stable power to each block including interfaces 2, 3, 21, microprocessor 1, input unit 4 and display unit 5.

A power controller 7 controls the voltage and current.

A voltage controller 8 controls the voltage.

A frequency controller 9 controls the frequency.

The power, voltage and frequency signals from the power controller 7, the voltage controller 8 and the frequency controller 9 are inputted into a power generation device 11, a light generation device 12 and a heat generation device 13, respectively, thereby generating power energy, light energy and heat energy.

The operations of the power controller 7, the voltage controller 8, the frequency controller 9 and the energy devices 11, 12 and 13 will be now be described in more detail.

Figure 4:
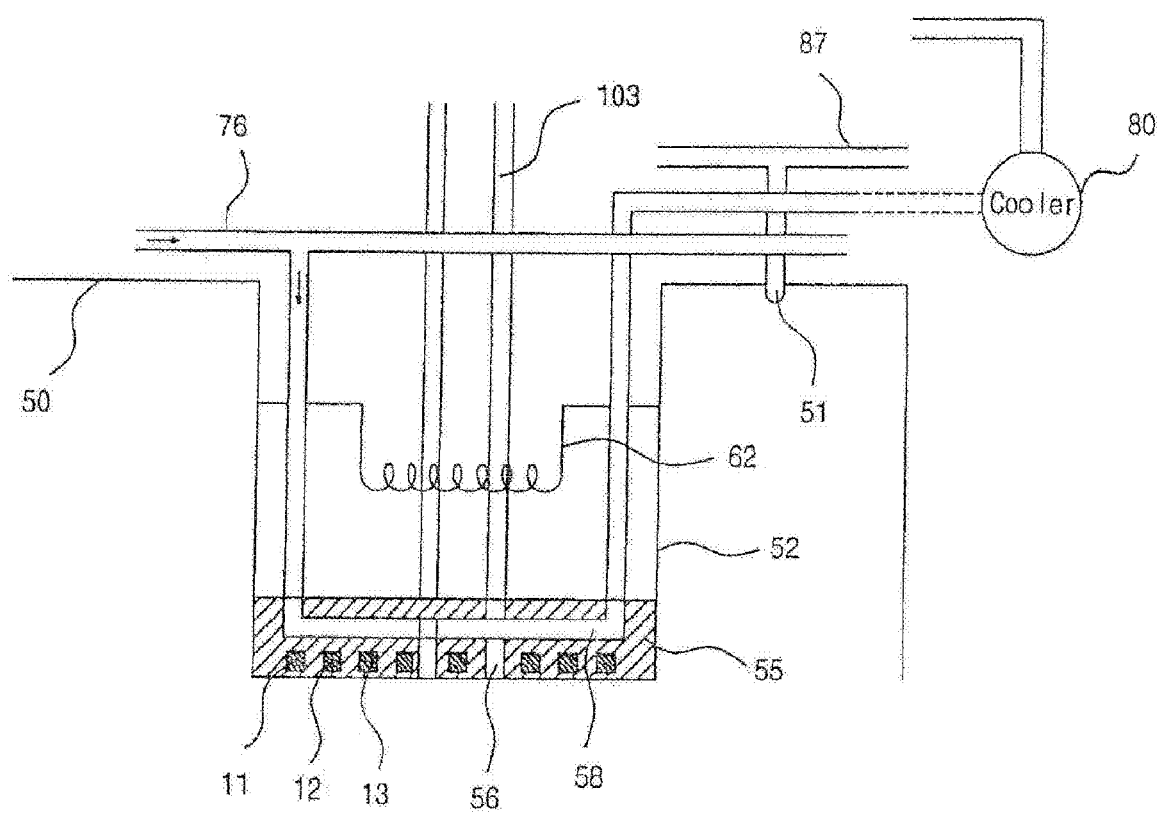
FIG. 4 is a cross sectional view of a head pin according to the present invention.

A control signal of the microprocessor 1 is sequentially inputted into the power controller 7, the voltage controller 8 and the frequency controller 9 through interface 2, thus controlling power, voltage and frequency, and applying these to energy generation device 11 to generate power energy. As shown in FIG. 4, a plurality of power generation devices 11 are provided in a touch panel 55 fixed to a lower side of the head pin 52, so that it works as a resistors, receiving power, voltage and frequency and generating voltage. The generated voltage is applied to a human body. Supplying the voltage to the human body helps blood circulation and stimulates nerves. An example voltage range is 0-750V and an example frequency range is 0-2 Ghz. These ranges may be changed for individual user, based on the user's condition.

The light generation device 12 may be formed of a light generation metal, tungsten, Na, semiconductor, or nonconductor. The heat generation device may be formed of a heat generation metal, tungsten Na, a semiconductor or a nonconductor.

The light generation device 12 and the heat generation device 13 receive the power, voltage and frequency controlled by the power controller 7, the voltage controller 8 and the frequency controller 9 and convert them into the light energy and heat energy.

The light generation device 12 and the heat generation device 13 may be selectively combined with each other.

The vibration controller 10 controls the vibration of a vibrator 30. The vibrator 30 is preferably provided in an upper side of the head housing 50. The head housing 50 is moved upward and downward, thus massaging a user's head.

A fault detector 14 adapted to find an error, etc provided. When an error occurs in each device, the detected error information is transferred to the interface 3. The detection value is transferred to the microprocessor 12 and displayed on display unit 5.

The output of sensor 15 is transmitted to the microprocessor 1. The microprocessor 1 compares the sensed value and a reference value, performs a computation and determines if the sensed value is within limits. The result of the detection is transmitted to the interface 2 or the interface 3 and displayed on display unit 5. The sensor 15 may be a current sensor, a voltage sensor, a frequency sensor, a temperature sensor, a moisture sensor, an approximate sensor (sensing distance to head hairs), a vibration sensor or other similar sensors.

The temperature controller 16 adjusts the temperature of the touch panel 55. The temperature control is performed by supplying water stored in a tank 72 using a pump 74. Water is supplied to a waterway 58 formed in the touch panel 55 of each head pin 52 through a discharge pipe 76. The water passed through the waterway 58 is transmitted through a cooler 80 through a suction pipe 78 and is cooled and sucked into the tank 72.

The discharge pipe 76 is connected with an entrance of a waterway of each touch panel 55. The suction pipe 78 is connected with an outlet of a waterway of each touch panel 55. Therefore, the discharge pipe 76 and the suction pipe 78 are separately connected. The cooler 80 is connected to suction pipe 78.

An anion air/oxygen generation controller 17 generates anion air or anion oxygen in the anion air/oxygen generator 85. The anion air/oxygen generator 85 is connected with a plurality of nozzles 51 provided in a lower side of the head housing 50 through a flow pipe 87 based on an operation of the pump 86, thus supplying anion air/oxygen.

A magnetic force generation controller 18 controls a magnetic force generator 62.

The magnetic force generator 62 located in an upper side of the touch panel 55 generates a magnetic force using a coil, providing the magnetic force to the user's hair.

Apparatus controller 19 controls an apparatus capable of supplying moisture or nutrition. For example, a nutrition supply apparatus 90 supplies nutrition to head hair based on the nozzles 51 using the flow pipe 87 through the pump 95.

In addition, a suction unit 98 sucks foreign substances from the head through the touch panel 55 and a suction port 56. The foreign substances are sucked into the suction tank 98 through the flow pipe 103 based on an operation of the pump 99.

A database 22 is connected with an external computer, thus communicating various data with the computer for driving the system. The data of the database 22 are processed by a remote control or manual computer control. All data can be shared or used by the users. The system can be easily managed and controlled, thus achieving an efficient management.

The data of the database 22 are converted into the signals needed by the interface 21 and are loaded into the microprocessor 1.

The major operations of the hair growth caring apparatus according to the present invention will now be described.

The head housing 50 covers the user's head, being supported by a certain support apparatus. The head housing 50 is formed of plastic.

First in Step S100 a check is made as to whether the power is on.

In Step S100, when the power is turned on, the hair growth caring apparatus according to the present invention performs a self-diagnosis in Step S102. At this time, as a result of the self-diagnosis, when the system is judged to be unstable, the routine is fed back to Step S100 for judging whether the power is turned on.

As a result of the self-diagnosis in Step S102, the data is stored in the database 22.

If the self-diagnosis in Step S102 indicates that the system is operational, a check is made in Step S106 to see, whether the system is set to the automatic mode.

In Step S106, when the mode is set to the automatic mode, the power, voltage, frequency, temperature, etc. and the anion air and oxygen generation states are operated based on the reference value stored in the database 22.

In Step S106, when the automatic mode is not selected, namely when the manual mode is selected, the microprocessor 1 outputs a control signal based on data from input unit 4, thus providing the signals to various controllers and the sensor 14.

In Step S112, a cheek is made as to whether the operation of the system is on or off.

In Step S112, when the system is operated, the microprocessor 1 operates in Step S114. At this time, the microprocessor 1 loads a set value from the database 22. When the mode is set to the manual mode, the data set through the input unit 4 is stored in Step S116.

In addition, in Step S120, the set value of the database 22 and the operation state of the system are displayed on the display unit 5, so that the users can check the operation states.

In Step S122, when the system operates in automatic operation mode, the microprocessor 1 that loads the set values stored in the database 22 performs a computation in Step S124.

When the system operates in automatic mode, the system is operated based on the value set by the user in Step S126.

During the operation, the user selectively operates the vibrator 30, the power generation device 11, the light generation device 12, the heat generation device 13, the temperature controller 16, the anion air/oxygen generator 85, the magnetic force generator 62, and other supply apparatuses through the input unit 4 in Step S218.

During operation, the operation of the system is checked through a detection unit such as the fault detector 14 or the sensor 15. Input data is applied to microprocessor 1 through interface 3, determining in Step S130 whether the system is in normal operation. If the system is operating normally, it is reported to the microprocessor 1.

In Step S130, if an error condition is detected, the detected data are transferred to the microprocessor 1 and the operation of the system may be stopped; the system state is displayed on the display unit 5.

In another embodiment of the present invention, one head pin 52 provided in a lower side of the head housing 50 contacts with a user's head wherein it is integral with the head housing 50, thus helping growth of the user's hair. In this embodiment of the present invention, the head housing and head pin are of a small size. Specifically, the power generation device 11, the light generation device 12, and the heat generation device 13 are all provided on the touch panel 55. In this embodiment, the touch panel 55 is cooled via an air cooling method, not a water cooling method. In addition, the temperature controller 16, the anion air/oxygen generator 85, the vibrator 30, the magnetic force generator 62, and other supply apparatuses are selectively provided.

INDUSTRIAL APPLICABILITY

As described above, in the present invention, it is possible to prevent side effects that may be caused by an artificial method such as depilation agents or hair transplantation by applying power energy, light energy and heat energy for a long time to a portion of the head where hairs are missing. In addition, it is possible to overcome the problems encountered in the conventional art. It is possible to achieve a natural hair growth for a depilation patient.

Since there are provided nutrition supply apparatuses and suction units in which vibration function and anion and air supply apparatuses and other apparatuses are combined, various functional processes are performed with respect to the hair, thus removing various waste materials and activating blood circulation and removing various bacteria.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

The invention claimed is:

1. A hair growth apparatus, comprising:
    a head housing;
    a plurality of head pins protruding from a lower side of the head housing;
    a touch panel fixed to a lower side of the plurality of head pins, the touch panel being cooled by air or water, and wherein a power generation device capable of generating electrical power, a light generation device capable of generating light, and a heat generation device capable of generating heat are fixed to the touch panel;
    a voltage regulator supplying electric power;
    a power controller controlling the power of the electric power supplied from the voltage regulator;
    a voltage controller controlling the voltage of the electric power supplied from the voltage regulator;
    a frequency controller controlling the frequency of the electric power supplied from the voltage regulator; and
    a microprocessor controlling the power, the voltage and the frequency respectively from the power controller, the voltage controller, and the frequency controller, wherein the microprocessor controls the power, the voltage, and the frequency to be applied to each of the power generation device, the light generating device, and the heat generation device.

2. The apparatus of claim 1, wherein a magnetic force generator is further provided in the plurality of head pins.

3. The apparatus of claim 1, wherein a suction port is provided in the touch panel for thereby sucking foreign substances from head skin using a pressure of a pump.

4. The apparatus of claim 1, wherein a plurality of nozzles are formed in a lower side of the head housing, and said plurality of nozzles supply anion air/oxygen from an anion air/oxygen generator and other supply apparatus through a flow pipe.

5. The apparatus of claim 1, wherein a vibrator is provided in an upper side of the head housing.

* * * * *